United States Patent [19]

Johnson, Jr. et al.

[11] 4,393,254

[45] Jul. 12, 1983

[54] PROCESS FOR THE PRODUCTION OF ALKYLENE GLYCOLS

[75] Inventors: Fred L. Johnson, Jr.; Lewis W. Watts, Jr., both of Austin, Tex.

[73] Assignee: Texaco Inc., White Plains, N.Y.

[21] Appl. No.: 224,412

[22] Filed: Jan. 12, 1981

[51] Int. Cl.³ .............................................. C07C 29/10
[52] U.S. Cl. .................................................... 568/867
[58] Field of Search ......................................... 568/867

[56] References Cited

U.S. PATENT DOCUMENTS 3,091,647  5/1963  Hamilton et al. .................... 568/867
3,851,043  11/1974  Gunther ......................... 568/867 X
4,014,945  3/1977  Zimmerschied et al. ............ 568/867
4,107,221  8/1978  Tasto et al. ...................... 568/867 X Primary Examiner—Bernard Helfin
Attorney, Agent, or Firm—Carl G. Ries; Jack H. Park; Kenneth R. Priem

[57] ABSTRACT

A process for the production of alkylene glycols is disclosed which comprises hydrating alkylene oxide in the presence of a partially amine-neutralized sulfonic acid catalyst.

8 Claims, No Drawings

PROCESS FOR THE PRODUCTION OF ALKYLENE GLYCOLS

BACKGROUND OF THE INVENTION

1. Field of the Invention

This invention relates to the field of alkylene glycol manufactured by catalytic hydration of alkylene oxide.

2. Description of the Prior Art

Prior art methods for hydrating alkylene oxides to the alkylene glycols include the direct hydration reaction without benefit of catalyst and the catalytic hydration of alkylene oxides using mineral acid catalysts. These mineral acid catalytic reactions are homogeneous thereby posing a problem for the commercial production of glycols since the catalyst is carried over into the product and must be separated. Present commercial processes use a noncatalytic hydration procedure which must use large ratios of water to alkylene oxide thereby presenting a problem of separation of the water from the finished product. This separation consumes large amounts of energy which recently has been the cause of much concern.

Recently, attempts have been made to discover a new catalyst for the hydration of alkylene oxides to the respective glycols. U.S. Pat. No. 4,160,116 describes such a method using quarternary phosphonium salts as catalyst. The prior art section of that patent describes the use of other catalysts, among them tetramethyl ammonium iodide and tetraethyl ammonium bromide, as disclosed in British Pat. No. 117,877. Other prior art catalytic processes using, for example, organic tertiary amines such as triethylamine and pyrridine are disclosed in German OLS No. 2,615,595.

A novel and highly effective catalyst for the hydration of alkylene oxides to the respective glycols has been discovered. This catalyst has advantages which include heterogeneity as well as the suppression of production of noxious dioxane.

SUMMARY OF THE INVENTION

The invention is a process for the production of alkylene glycol in which the hydration of an alkylene oxide is carried out in the presence of a catalytic quantity of a heterogeneous, partially amine-neutralized sulfonic acid catalyst. Alkylene glycols are useful, for example as freezing point depressants.

DESCRIPTION OF THE PREFERRED EMBODIMENTS

We have discovered that a partially amine neutralized sulfonic acid catalyst promotes the selective formation of alkylene glycol from the hydration of alkylene oxides even when very low mol ratios of water and alkylene oxides are employed as the reactants. Also, this catalyst does not produce measurable quantities of noxious dioxane.

The alkylene oxides useful in the practice of this invention are the lower alkylene oxides having 2 to 4 carbon atoms, especially ethylene oxide and propylene oxide. An especially preferred embodiment of this invention is the catalytic hydration of ethylene oxide.

The catalysts useful in the practice of this invention are partially amine-neutralized sulfonic acid catalysts. These catalysts are heterogeneous and may be described more completely as sulfonic acid-type ion exchange resins. These resins are then modified by passing sufficient amine through the resin to partially neutralize the sulfonic acid groups contained therein. Primary, secondary or tertiary amines are each acceptable. Tertiary amines are preferred for this invention. The result is a catalyst which consists of a mixture of the original free sulfonic acid and the amine salt of the sulfonic acid, all still in the heterogeneous form.

An especially preferred catalyst comprises a styrene-divinylbenzene copolymer matrix with pendant sulfonic acid groups. Catalysts falling within this preferred species are available from Rohm and Haas under the designation Amberlyst ® 15 and Amberlyst XN-1010 which differ in the amount of surface area available.

Other matrices than the styrene-divinylbenzene type could be used, including other organic polymers and inorganic materials, provided only that the substrate be capable of binding the sulfonic acid groups to maintain a heterogeneous catalyst system.

The amount of amine neutralization necessary depends on the constituents and the desired rate of reaction. More neutralization will result in less dioxane production but less catalytic activity. No set amount of neutralization can be specified. The amount which reduces dioxane production to a desired amount and yet retains sufficient catalytic activity to be useful is desirable.

The temperature range useful in the process of this invention is from about 100° to 200° C. It is preferred to use a temperature of about 100° to 125° C. The pressure may range upward from a lower limit which is the pressure necessary to maintain the alkylene oxide in a liquid phase at the highest temperature within the reactor. This temperature is generally referred to as the "hot spot" temperature. The reaction pressure will vary, of course, according to the reactor temperature and the stage at which the reaction was attained. However, as a general guideline the pressure may vary from about 200 to 1000 psi. It is preferred to operate within a pressure range of about 200 to about 400 psi.

It has been discovered, as the following data will show, that the selectivity to alkylene glycol remains very high even when low water-to-alkylene-oxide ratios are employed. Commercial processes using uncatalyzed hydration of ethylene oxide use from about 12 to 20 mols of water per mol of ethylene oxide. The process of our invention uses mol ratios of water-to-alkylene-oxide which vary from about 2 to about 10. Preferably, the mol ratio of water-to-ethylene oxide should be about 2–5.

The presence of carbon dioxide is optional and does not affect the hydration reaction.

In a particularly preferred embodiment of this invention, water and ethylene oxide are contacted with a heterogeneous sulfonic acid type ion exchange resin which has been partially neutralized with a tertiary amine. The mol ratio of water to ethylene oxide is about 3. The pressure is about 300 psig, and the temperature is about 110° C.

The following examples are illustrative of the invention but are not intended to limit it.

EXAMPLE I

The reactor consisted of a 1"×30" stainless steel tube containing a heterogeneous catalyst Amberlyst XN-1010 surrounded by a jacket containing refluxing toluene for heating and cooling. Reactor pressure was maintained at 300 psig by a "Mitey-Mite" back pressure regulator, thus assuring liquid phase operation. Water and ethylene oxide feeds to the reactor were pumped as liquids and entered the reactor at the bottom for upflow operations. A thermowell, the full length of the catalyst bed, ran up the center of the reactor tube and contained five thermocouples, equally spaced, for monitoring reactor temperatures. $CO_2$ feed was a gas and was metered with a mass flowmeter/controller. A composite sample collected over a period of one hour was analyzed by gas chromatography as area percent on a water free basis.

Conditions

Catalyst—Amberlyst XN-1010 which had been 50% neutralized by reaction with triethylamine.

| Reactor jacket temperature | 110° C. |
|---|---|
| Reactor hot spot | 115° C. |
| Reactor pressure | 300 psig |
| Mol ratio H₂O/ethylene oxide | 3.0 |
| Liquid hourly space velocity (LHSV) | 1.3 g feed/cc catalyst/hour |
| Mol ratio CO₂/ethylene oxide | 0.1 |

Results Area percent by gas chromatography (H₂O free basis)

| Ethylene glycol | 87.8 | |
|---|---|---|
| Diethylene glycol | 8.7 | |
| Triethylene glycol | 0.6 | EO Conversion 71% |
| Higher glycols | 0.1 | |
| Unknowns | 2.9 | |

EXAMPLE II

The apparatus and procedure used is described in Example I. The only difference was that the catalyst in this example had not been treated with triethylamine. Note the fact that even with a higher H₂O/ethylene oxide mol ratio (10.7 vs 3.0), the hot spot in the resin was much higher (140°–145° C. vs 115° C.). The ethylene oxide conversion was higher (probably due to the higher temperature) but the selectivity to ethylene glycol was lower (82.1% vs 87.8%).

Conditions

| Catalyst | Unmodified Amberlyst XN-1010 |
|---|---|
| Reactor jacket temp. | 110° C. |
| Reactor hot spot temp. | 140–145° C. |
| Reactor pressure | 300 psig |
| Mol ratio H₂O/EO | 10.7 |
| Mol ratio CO₂/EO | 0.1 |
| LHSV | 2.3 |

Results: Area percent by gas chromatography (H₂O free basis)

| Ethylene glycol | 82.1 | |
|---|---|---|
| Diethylene glycol | 12.8 | EO conversion 100% |
| Triethylene glycol | 2.6 | |
| Higher glycols | 2.4 | |

EXAMPLE III

This run represents the prior art (non-catalytic). The same apparatus was used as in Example I, except no CO₂ was fed. Instead of a catalyst, the reactor tube was packed with 3 mm Pyrex® glass beads. Note the higher mol ratio H₂O/EO (7.6 vs 3.0), the higher reactor temperatures (140° vs 115° C.), and the 77% conversion.

Conditions

| Catalyst | None |
|---|---|
| Reactor jacket temperature | 140° C. |
| Reactor hot spot temperature | 140° C. |
| Reactor pressure | 200 psig |
| Mol ratio H₂O/EO | 7.6 |
| Mol ratio CO₂/EO | 0 |
| LHSV | 1.7 |

Results: Area percent by gas chromatography (H₂O free basis)

| Ethylene glycol | 81.8 | |
|---|---|---|
| Diethylene glycol | 15.5 | EO Conversion 77% |
| Triethylene glycol | 2.2 | |
| Higher glycols | 0.6 | |

We claim:

1. A process for the production of alkylene glycol which comprises contacting water and an alkylene oxide in the presence of a heterogeneous catalyst comprising a partially amine-neutralized sulfonic acid resin wherein the mole ratio of alkylene oxide to water ranges from about 2 to about 10, the temperature of reaction ranges from about 100° to 200° C. and the reaction pressure ranges from about 200 to 400 psi.

2. A process for the production of alkylene glycol which comprises contacting water and an alkylene oxide in the presence of a heterogeneous catalyst comprising a partially amine-neutralized sulfonic acid resin wherein the mole ratio of alkylene oxide to water ranges from about 2 to 5, the temperature of reaction ranges from about 100° to about 125° C. and the reaction pressure ranges from about 200 to 400 psi.

3. A process for the production of alkylene glycol which comprises contacting water and an alkylene oxide in the presence of a heterogeneous catalyst comprising a partially amine neutralized styrene-divinylbenzene copolymer having pendant sulfonic acid groups wherein the mole ratio of alkylene oxide to water ranges from about 2 to about 10, the temperature of reaction ranges from about 100° to about 200° C. and the reaction pressure ranges from about 200 to 400 psi.

4. A process for the production of alkylene glycol which comprises contacting water and an alkylene oxide in the presence of a heterogeneous catalyst comprising a partially amine neutralized styrene-divinylbenzene copolymer having pendant sulfonic acid groups wherein the mole ratio of alkylene oxide to water ranges from about 2 to 5, the temperature of reaction ranges from about 100° to about 125° C. and the reaction pressure ranges from about 200 to 400 psi.

5. A process for the production of ethylene glycol which comprises contacting water and ethylene oxide in the presence of a heterogeneous catalyst comprising a partially amine-neutralized sulfonic acid resin wherein the mole ratio of alkylene oxide to water ranges from about 2 to about 10, the temperature of reaction ranges from about 100° to about 200° C. and the reaction pressure ranges from about 200 to 400 psi.

6. A process for the production of ethylene glycol which comprises contacting water and ethylene oxide in the presence of a heterogeneous catalyst comprising a partially amine-neutralized sulfonic acid resin wherein the mole ratio of alkylene oxide to water ranges from about 2 to 5, the temperature of reaction ranges from about 100° to about 125° C. and the reaction pressure ranges from about 200 to 400 psi.

7. A process for the production of ethylene glycol which comprises contacting water and an ethylene oxide in the presence of a heterogeneous catalyst comprising a partially amine neutralized styrene-divinylbenzene copolymer having pendant sulfonic acid groups wherein the mole ratio of alkylene oxide to water ranges from about 2 to about 10, the temperature of reaction ranges from about 100° to about 200° C. and the reaction pressure ranges from about 200 to 400 psi.

8. A process for the production of ethylene glycol which comprises contacting water and an ethylene oxide in the presence of a heterogeneous catalyst comprising a partially amine neutralized styrene-divinylbenzene copolymer having pendant sulfonic acid groups wherein the mole ratio of alkylene oxide to water ranges from about 2 to 5, the temperature of reaction ranges from about 100° to about 125° C. and the reaction pressure ranges from about 200 to 400 psi.

* * * * *